United States Patent
Buehring et al.

(10) Patent No.: US 7,182,946 B2
(45) Date of Patent: Feb. 27, 2007

(54) ANTIBODIES ISOLATING AND/OR IDENTIFYING NEURONAL STEM CELLS AND METHOD FOR ISOLATING AND/OR IDENTIFYING NEURONAL PROGENITOR CELLS

(75) Inventors: Hans-Joerg Buehring, Tuebingen (DE); Wichard Vogel, Tuebingen (DE)

(73) Assignee: Eberhard-Karls-Universitaet Tuebingen Universitaetsklinikum, Tuebingen (DE)

(*) Notice: Subject to any disclaimer, the term of this patent is extended or adjusted under 35 U.S.C. 154(b) by 0 days.

(21) Appl. No.: 11/076,793

(22) Filed: Mar. 9, 2005

(65) Prior Publication Data

US 2005/0214872 A1     Sep. 29, 2005

Related U.S. Application Data

(63) Continuation of application No. PCT/EP03/09894, filed on Sep. 5, 2003.

(30) Foreign Application Priority Data

Sep. 9, 2002  (DE) .................. 102 42 337

(51) Int. Cl.
  *A61K 39/395*   (2006.01)
  *C07K 16/28*   (2006.01)
  *G01N 33/53*   (2006.01)

(52) U.S. Cl. .................. 424/141.1; 435/7.21; 435/368; 530/388.1

(58) Field of Classification Search ...................... None
See application file for complete search history.

(56) References Cited

FOREIGN PATENT DOCUMENTS

EP    0 889 054    1/1999

OTHER PUBLICATIONS

Alberts et al. 1994. Molecular Biology of the Cell, 3rd Edition, pp. 186-188.*
Nicolet 1997. Tumor Biology 18:356-366.*
Muraro 1988. Cancer Research 48:4588-4596.*
Barami et al., Neurological Research (2001) 23:321-326.
Brazelton et al., Science (2000) 290:1775-1779.
Clarke et al., NeuroReport (1994) 5:1885-1888.
Giesert et al., Annals New York Acadamy of Sciences (2001) 938:175-183.
Hu et al., Leuk. Res. (1998) 22:817-826.
Kohler and Milstein, Nature (1975) 256:495-497.
Kopen et al., PNAS USA (1999) 96:10711-10716.
Magrassi, Haematologica (2003) 88:121.
Rao, Anatomical Record (1999) 257:137-148.
Sejersen and Lendahl, J. of Cell Science (1993) 106:1291-1300.
Vogel et al., Haematologica (2003) 88:126-133.
Wei et al., Stem Cells (2000) 18:409-414.
Woodbury et al., J. of Neuroscience Research (2000) 61:364-370.

* cited by examiner

*Primary Examiner*—Robert C. Hayes
*Assistant Examiner*—Daniel E. Kolker
(74) *Attorney, Agent, or Firm*—Klarquist Sparkman LLP

(57) ABSTRACT

The present invention relates to mono clonal antibodies or fragments thereof for isolating and/or identifying neural progenitor cells. The antibodies or fragments thereof bind to an identical antigen as an antibody which is produced by the hybridoma cell lines W4A5, W8C3 and 57D2 deposited on Aug. 14, 2002, at the Deutsche Sammlung von Mikroorganismen und Zellkulturen (DSMZ) under the numbers DSM ACC2571, DSM ACC2570 and DSM ACC2568.

7 Claims, 1 Drawing Sheet

ANTIBODIES ISOLATING AND/OR IDENTIFYING NEURONAL STEM CELLS AND METHOD FOR ISOLATING AND/OR IDENTIFYING NEURONAL PROGENITOR CELLS

CROSS REFERENCES TO RELATED APPLICATIONS

This application is a continuation of copending international application PCT/EP03/09894 filed on Sep. 5, 2003 and designating the U.S., which was not published under PCT Article 21(2) in English, and claims priority of German patent application DE 102 42 337.7 filed on Sep. 9, 2002, which is incorporated herein by reference.

BACKGROUND OF THE INVENTION

1. Field of the Invention

The present invention relates to mono clonal antibodies for isolating and/or identifying neural progenitor cells.

2. Related Prior Art

In contrast to many other tissues, the central nervous system has only a limited regeneration potential. Mature nerve cells which have died are not regenerated. Although neural stem cells are in fact present in the adult central nervous system (CNS), they have only a limited capacity to generate new, functionally active nerve cells after injuries.

There is for this reason great interest in the possibility of repairing the nervous system by transplanting new cells which can replace cells which have been lost through injury or disease.

At present, no suitable possibilities for remediation in particular of diseases or injuries associated with neurological deficits are available. Examples of such diseases are Parkinson's disease, Huntington's chorea, Alzheimer's disease, epilepsy, strokes or spinal cord injuries. Currently, transplantation appears to be the most promising form of therapy.

Because of the highly complicated architecture of the brain and the complex connections of the individual regions of the brain, cell replacement strategies in the nervous system make use of immature progenitor cells which must become incorpo-rated into the existing structures and do not differentiate until there.

Multipotent stem cells with the capacity of differentiating into neural cells have been found inter alia in the human central nervous system. Such neural progeni-tor cells express nestin as typical surface marker and are able to differentiate for example into neurons, oligodendrocytes and astrocytes.

Rao M S., "Multipotent and restricted precursors in the central nerv-ous system", Anat. Rec. 257: 137 148 (1999), was able to isolate multipotent progenitor cells from adult human brain regions, including inter alia the temporal and frontal regions, the tonsils and the hippocampus. Moreover, Barami et al., "An efficient method for the culturing and generation of neurons and astrocytes from second trimester human central nervous system tissue", Neurol. Res. 23: 321 326 (2001), showed that neural progenitor cells (NPC) from the central nervous system of human fetal tissue were CD133-positive and in addition were able to differentiate with epidermal growth factor (EGF), fibroblast growth factor and leukemia-inhibiting factor in vitro into neurons and astrocytes.

The cell surface marker CD133 was originally found on hematopoi-etic stem and progenitor cells, but more recent studies have shown that this marker is also expressed in various neural tissues and skeletal muscle tissues. For these reasons, this marker on its own is unsuitable for the purposes of distinguishing different stem or pro-genitor cells.

A great problem in the identification of neural progenitor cells is that neural progenitor cells and mesenchymal stem cells represent homogeneous populations in terms of morphology and phenotype. This is attributable in particular to the limited number of antigens investigated and identified to date.

Mesenchymal stem cells can be obtained and isolated from the bone marrow of adult humans. They are multipotent and contribute to the regeneration of bone, cartilage, tendons, muscles, adipose tissue and stroma.

Kopen et al., "Marrow stromal cells migrate throughout forebrain and cerebellum, and they differenciate into astrocytes after injection into neonatal mouse brains", Proc. Nat. Acad. Sci. USA, 96: 10711 10716 (1999) and Brazelton et al., "From marrow to brain: expression of neuronal phenotypes in adult mice", Science 290: 1775 1779 (2000), were in fact able to show that mesenchymal stem cells isolated from bone marrow were able to differentiate also into non-mesenchymal cells such as liver cells, neural and glial cells. In addition, it has been possible to show only recently that mesen-chymal stem cells from adult human bone marrow were able to differentiate into neural cells in vitro. Woodbury et al., "Adult rat and human bone marrow stromal cells differen-ciate into neurons", J. Neurosci. Res. 61: 364 370 (2000), showed that in the presence of dimethyl sulfoxide (DMSO) and β-mercaptoethanol (BME) mesenchymal stem cells were able to differentiate into cells which expressed neurofilament and neuron-specific enolase.

Other research groups describe the differentiation of stromal bone marrow cells by means of epidermal growth factor and brain-derived neurotrophic factor (BDNF) into nerve cells which expressed nestin, glial fibrillary acidic protein (GFAP) and the neuron-specific nuclear protein (Neu N).

The fact that mesenchymal stem cells can also differentiate under certain conditions into nerve cells gives rise to the need to be able to distinguish neural progenitor cells from mesenchymal stem cells.

Despite the great interest, research on these neural progenitor cells has been greatly impaired by the lack of unambiguously defined markers for these cells. It is precisely the ability to identify relevant types of cells which first makes it possible to analyze the way in which the various cell populations of the central nervous system are generated.

Markers which are employed in particular for neural progenitor cells are antibodies against the protein nestin which is typically expressed by neural progenitor cells. However, this protein is also expressed by other cells such as, for example, astrocytes (see Clarke et al., "Reactive astrocytes express the embryonic intermediate neurofilament nestin", Neuroreport 5: 1885 1888 (1994)) and muscle cells (see Sejersen and Lendahl, "Transient expression of the intermediate neurofilament nestin during skeletal muscle development", J. Cell Sci. 106: 1291 1300 (1993)).

For these reasons, immunoreactivity with nestin is unsuitable as sin-gle criterion for identifying a particular cell as neural progenitor cell.

SUMMARY OF THE INVENTION

Against this background, it is an object of the present invention to provide mono clonal antibodies with which it is possible to identify and, where appropriate, to separate neural progenitor cells for example from a sample of a cell suspension.

This object is achieved according to the invention by an antibody or a fragment thereof which binds to the same antigen as an antibody produced by a hybri-doma cell line which is selected from the group consisting of the following hybridoma cell lines: W4A5, W8C3 and 57D2 which were deposited on Aug. 14, 2002, at the Deutsche Sammlung von Mikroorganismen und Zellkulturen (DSMZ) Mascheroder Weg 1b, D-38124 Braunschweig, Germany, in accordance with the Budapest Treaty under the numbers SDM ACC2571, DSM ACC2570 and DSM ACC2568.

The object underlying the invention is completely achieved thereby.

The inventors were able to show in their own experiments that it is possible with the novel antibodies of the invention to isolate and to characterize neural progenitor cells in a selective manner.

The inventors have additionally succeeded in distinguishing neural progenitor cells from, for example, mesenchymal stem cells, with the aid of the novel antibodies in an outstanding fashion.

Another object of the present invention is an antibody or a fragment thereof which is produced by the hybridoma cell line W4A5 which was deposited in accordance with the Budapest treaty on Aug. 14, 2002, at the Deutsche Sammlung von Mikroorganismen und Zellkulturen (DSMZ) under the number DSM ACC2571.

A further object of the present invention is an antibody or a fragment thereof which is produced by the hybridoma cell line W8C3 which was deposited in accordance with the Budapest treaty on Aug. 14, 2002, at the Deutsche Sammlung von Mikroorganismen und Zellkulturen (DSMZ) under the number DSM ACC2570.

An additionally object of the present invention is an antibody or a fragment thereof which is produced by the hybridoma cell line 57D2 which was deposited in accordance with the Budapest treaty on Aug. 14, 2002, at the Deutsche Sammlung von Mikroorgranismen und Zellkulturen (DSMZ) under the number DSM ACC2568.

The inventors were able to generate the antibodies W8C3 and W4A5 by using the cell line WERI RB 1.

This cell line is a cell line isolated from a retinoblastoma and has, for example, the number DSMZ ACC 90 in the Deutsche Sammlung von Mikroorganismen und Zellkulturen. It was not to be expected—and there was no indication thereof in the art either—that it is possible with use of this cell line to generate antibodies for identifying neural progenitor cells.

The antibody 57D2 was generated by using the cell line TF 1.

This cell line is an erythroleukemia cell line which has for example the number DSMZ ACC 334 at the Deutsche Sammlung von Mikroorganismen und Zellkulturen. There is no evidence in the literature that it is possible by using this cell line to generate antibodies which are specific for neural progenitor cells and are therefore suitable for the identification and/or isolation thereof.

To this extent it was surprising that the antibodies W8C3, W4A5 and 57D2 bind to antigens which are characteristic of neural progenitor cells to such an extent that they provide an excellent opportunity for selective identification of neural progenitor cells from a sample comprising various cell populations. The cell lines used for immuniza-tion are already differentiated, which is why it was not to be expected that a multipotent neural progenitor cell would be recognized by the antibodies of the invention on the basis of its different surface markers.

The production of mono clonal antibodies by fusion of spleen cells from immunized mice and myeloma cells was described in 1975 by Kohler and Milstein ("Continuous cultures of fused cells secreting antibody of predefined specificity", Nature 256: 495 497). The techniques for the chemical selection of the hybridomas resulting from such a fusion, and the subsequent isolation of cell clones which secrete single antibodies for the production of mono clonal antibodies are likewise known in the art.

The inventors have been able to show in their own experiments that the abovementioned antibodies are specific for neural progenitor cells. The inventors were additionally able to show in their own experiments that neural progenitor cells which have a known immunophenotype (in each case positive for CD15, CD56, CD90, CD133, CD164, CD172a, NGFR (neural growth factor receptor)) could be fractionated into subpopulations using the novel antibodies.

For the purposes of the present invention it is possible to use instead of the respective antibody mentioned also a fragment of the antibody without this being expressly mentioned in each case. "Fragment" means in this connection any fragment of an antibody retaining the antigen-binding function of the antibody. Examples of such fragments are Fab, F(ab')2, Fv and other fragments such as CDR fragments. Said fragments display the binding specificity of the antibody and can also be produced for example by known methods.

The antibodies of the invention also make it possible now to produce further antibodies which bind to the same antigen. Through the antibodies of the invention it is possible to isolate the corresponding antigenic structure using generally known methods, and to develop further mono clonal antibodies against the same antigenic structure, known methods also being used in this case.

Another object of the present invention is a hybridoma cell line which has the ability to produce and release such antibodies, and in particular the hybridoma cell lines W8C3, W4A5 and 57D2.

The inventors have used the novel antibodies to produce for the first time mono clonal antibodies, and hybridoma cell lines producing and releasing them, which make specific recognition of neural stem cells possible. The antibodies thus represent a means which is unique to date for the physician and researcher on the one hand to detect such cells, and on the other hand where appropriate to manipulate these cells, either through the antibody itself or through reagents coupled thereto.

A further object of the present invention is a method for isolating and/or identifying neural stem cells, in which method there is use of an antibody or a fragment thereof which binds to the same antigen as an antibody produced by a hybridoma cell line which is selected from the group of the following hybridoma cell lines 57D2, W8C3 and W4A5 which were deposited on Aug. 14, 2002, at the DSMZ in accordance with the Budapest treaty under the numbers DSM ACC2571, DSM ACC2570 and DSM ACC2568.

The antibodies or fragments thereof particularly used in this connec-tion are those produced by a hybridoma cell line which is selected from the group of the following hybridoma cell lines 57D2, W8C3 and W4A5 which were deposited on Aug. 14, 2002 at the DSMZ in accordance with the Budapest treaty under the numbers DSM ACC2571, DMS ACC2570 and DSM ACC2568.

The inventors have realized that it is possible with the method of the invention in particular for neural progenitor cells to be identified and, for example, differ-entiated from mesenchymal stem cells.

Another object of the present invention is a method for identifying neural progenitor cells with an antibody, which method includes the following steps:

contacting a sample of a cell suspension which comprises neural progenitor cells to the novel mono clonal antibodies or fragments thereof, and identifying those cells in the sample which bind to the novel mono-clonal antibodies or fragments thereof.

An additional object of the present invention is a method for isolat-ing neural progenitor cells with an antibody, comprising the following steps:

contacting a sample of a cell suspension which comprises neural progenitor cells to the novel mono clonal antibodies or fragments thereof, and isolating from the sample those cells which bind to the novel mono-clonal antibody or to a fragment thereof.

The sample can be selected from any source which comprises neural stem cells, for example a sample from the bone marrow or peripheral blood. These cells are obtained by laboratory methods known in the art and are in many cases commercially available.

The contacting of a sample of a cell suspension which comprises neural stem cells can moreover take place in solution, as is the case for example on use of a flow cytometer (=fluorescent-activated cell sorter (FACS)).

In flow cytometry, cells are loaded with antibodies which are, on the one hand, specific for a surface marker and, on the other hand, coupled to a fluorescent dye. Cells which are marker-positive fluoresce, whereas the negative cells remain dark. It is thus possible to establish which portion of a cell population is marker-positive. At the same time, a flow cytometer allows the size and granularity of cells to be determined.

It is also possible to employ a method of magnetic cell separation (MACS, magnetic cell sorting). In this method, the cells are labeled with magnetic beads, it being possible for these beads to be coupled for example to the antibodies.

The contacting can also be carried out by immobilizing the mono-clonal antibody on a carrier as this is the case for example in column chromatography.

The cell suspension may be any solution with bone marrow cells, blood cells or tissue cells.

After the cell suspension has been mixed with the antibody, the cells which express the relevant antigen bind to the antibody, after which these cells can be identified and/or isolated from the cells which have not bound to an antibody by the described method.

The neural progenitor cells which have been identified/isolated in this way can then be employed for example for transplantation in order to achieve regeneration of neurological damage.

The invention relates further to the use of a novel antibody or of a fragment thereof for identifying neural progenitor cells.

The invention further relates to the use of the cell line TF 1 for pro-ducing antibodies or fragments thereof for isolating and/or identifying neural progenitor cells.

The invention additionally relates to the use of the cell line WERI-RB 1 for producing antibodies or fragments thereof for isolating and/or identifying of neural progenitor cells.

A further object of the present invention is a pharmaceutical compo-sition comprising one or more of the above-mentioned antibodies of the invention.

Such a pharmaceutical composition may, besides the one or more antibodies, comprise further suitable substances such as, for example, diluents, solvents, stabilizers etc. These include for example physiological saline solutions, water, alcohols, and further suitable substances which are to be found for example in A. Kibble, "Hand-book of Pharmaceutical Excipients", 3rd ed., 2000, American Pharmaceutical Association and Pharmaceutical Press.

An additional object of the present invention is a kit which comprises at least one of the novel antibodies.

Further advantages are evident from the appended figures and the description.

It will be appreciated that the features mentioned above and to be explained hereinafter can be used not only in the combination indicated in each case, but also alone or in other combinations, without leaving the scope of the present invention.

BRIEF DESCRIPTION OF THE FIGURE

Exemplary embodiments are depicted in the appended drawing and are explained in detail in the description. This shows:

FIG. 1 FACS analyses which show that neural progenitor cells ex-press CD15, CD56, CD90, CD133, CD164, CD172a;

DESCRIPTION OF PREFERRED EMBODIMENTS

Material and Methods

Figure 1:
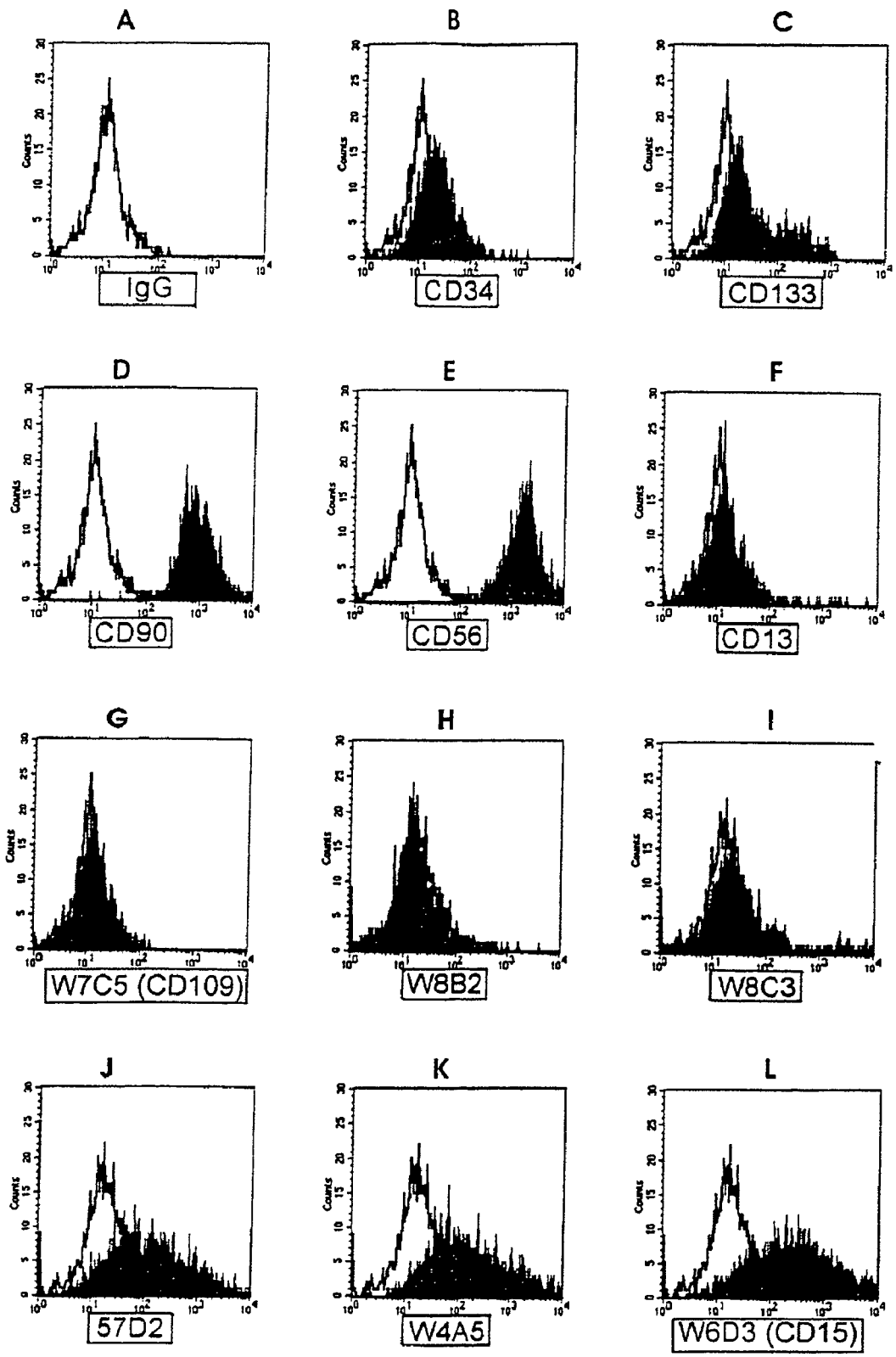

Neural progenitor cells were purchased from CellSystems, St. Katharinen, Germany.

The following mono clonal antibodies or antibody conjugates were employed for the fluorometric analyses: W8B2, W8C3, W4A5 and W7C5 (CD109), all of which were obtained starting from the retinoblastoma cell line WERI RB 1. This cell line is obtainable from the DSMZ under the number ACC90.

The mono clonal antibody 57D2 which was obtained by immunizing mice with the TF 1 erythroleukemia cell line (DSMZ: ACC334) were additionally em-ployed.

The antibodies of known specificities employed were CD10 PE, CD13 PE, CD34 PE, CD45 PE, CD56 PE, CD61 PE, CD117 PE (all obtainable from Becton Dickinson, Heidelberg, Germany). PE (phycoerythrin)-conjugated mono clonal antibodies with a specificity for CD90, CD140B and CD164 were obtained from PharMin-gen (San Diego, USA). The antibody against the nerve growth factor receptor (NGFR) was purchased from Sigma (Munich, Germany). CD133 PE (clone W6B3C1), CD167a (clone 48B3), CD172a PE (clone SE5A5), the CD15 specific antibody W6D3 and the CD105 specific mono clonal antibody 43A3 were produced in the inventor's laboratory. Unconjugated antibodies were stained using isotype-specific PE-conjugated goat anti-mouse antisera (Southern Biotechnology Associates, Inc., Birmingham, USA).

Staining of Cells and Flow Cytometry

For the cytometric analyses, the commercially available neural pro-genitor cells (NPC) were incubated with 10 µl of phycoerythrin-conjugated antibodies or 25 µl of culture supernatant in 96 well microtiter plates at 4° C. for 20 minutes. Unconju-gated mono clonal antibodies were stained after a washing step in FACS buffer (PBS; 0.5% BSA; 0.1% NaN3) using goat anti-mouse IgG1 PE (1:100) or goat anti-mouse IgG3 PE (1:20) antisera. After a further washing step, the cells were analyzed with a flow cytometer (FACSCalibur, Becton Dickinson) using the Cell Quest software (Bacton Dickinson).

For the immunocytochemical analysis of intracellular antigens and extracellular matrix proteins, the neural progenitor cells were fixed on 8 well chamber slides with acetone for 2 minutes and labeled with the primary antibody for 60 minutes. Staining was then carried out with Alexa 488 conjugated goat anti-mouse IgG or goat anti-rabbit IgG antisera. For the controls, the cells were labeled either with an isotype-matching control antibody or with a preimmune rabbit serum. The fluorescence of the cells was evaluated using a fluorescence microscope (Zeiss, Oberkochen, Germany).

Results

Immunophenotype of Neural Progenitor Cells

Commercially available fetal neural progenitor cells (NPC hereinaf-ter) (CellSystems, St. Katharinen, Germany) were investigated for their immunophenotype.

It was possible to detect two NPC populations differing in size in a double scatter plot. Large NPC showed stronger CD133, CD172a and W8C3 antigen expression than the smaller NPC, whereas CD13 was identified principally on a small NPC subpopulation. All NPC subpopulations expressed CD56, CD90, CD164, NGFR and the antigens to which the antibodies 57D2, W4A5, W6D3 (CD15) produced by the inventors bind. These cells were negative for CD45, CD105 (endoglin) and CD140b (PDGF RB), as well as for the antigens W7C5 (CD109) and W8B2.

FIG. 1 depicts selected examples of these analyses. It is unambigu-ously evident from histograms D and E in FIG. 1 that the NPC are positive for CD90 and CD56, while histograms I, J, K and L in FIG. 1 depict the positive results for W8C3, 57D2, W4A5 and W6D3 (CD15).

The extent to which the novel antibodies bind for example to mesen-chymal stem cells was investigated in other experiments. On the one hand, mesenchymal stem cells isolated by the inventors from bone marrow cells from the pelvic cavity of volunteer donors and, on the other hand, mesenchymal stem cells which can be purchased (CellSystems, St. Katharinen, Germany) were employed for this. In most cases, the expres-sion pattern of the commercial mesenchymal stem cells and that of the mesenchymal stem cells isolated by us (hereinafter: MSC) were identical or similar. The MSC proved to be unambiguously negative for W4A5, W6D3 and CD133 and only a small subpopulation of the MSC showed a weakly positive reaction for 57D2.

The results of the investigations are summarized in table 1 below, there having been investigation in this case of the antigen expression on commercially obtained neural progenitor cells (NPC, comm.) and that on mononuclear cells from the bone marrow of healthy donors (BMMNC).

The meanings in the table are − negative, i.e. no expression on the relevant cells, + positive, i.e. expression on the cells, (+) positive at least in one analysis, S slight to undetectable expression, P cell population <5%.

| Antigen/antibody | NPC comm. | BMMNC |
|---|---|---|
| CD13 | P | P |
| CD34 | S | P |
| CD45 | − | + |
| CD56 | + | P |
| CD90 | + | P |
| CD105 | − | P |
| CD117 | S | P |
| CD133 | + | p |
| CD140B | − | P |
| CD164 | + | + |
| CD167 | S | − |
| CD172a | + | + |
| W4A5 | + | − |
| W6D3 (CD15) | + | + |
| W7C5 (CD109) | − | P |
| W8B2 | − | − |
| W8C3 | P | − |
| 57D2 | + | − |
| NGFR | + | − |

Comparing with BMMNC, therefore, NPC expressed the antigens of the novel antibodies W4A5, 57D2 and W8C3 and consisted mainly of a CD133$^+$ population (25–40% compared with <1% BMMNC).

The growth of neurospheroids was observable on cultivation of the NPC in serum-free media in the presence of neural progenitor cell medium (CellSystems). In the presence of 10% fetal calf serum (FCS) and in the absence of growth factors, the spheres adhered to the plastic surface of the culture dishes. NPC cultivated in growth medium for astrocytes differentiated into astrocytes with long pseudopods. NPC kept on chamber slides in the presence of astrocyte medium expressed nestin, MAP2, neurofila-ments, GFAP, W4A5 and β2-chain laminin.

Summary

Stem cells of the central nervous system such as neural progenitor cells represent in relation to therapeutic uses an important source for developing strategies for therapies to restore injured or diseased brain tissue. NPC can be isolated both from adult and from fetal brain. A large subpopulation of these cells is CD133 positive and negative for CD34, CD45 and CD24. In culture, these cells differentiate into neurospheres.

NPC has proved to be positive for CD56, CD90, CD133, W4A5, W6D3 (CD15), W8C3 and 57D2, and negative for CD45, CD10, W7C5 (CD109) and W8B2. Similar to the NPC expressed bone marrow subpopulations CD133, CD56, CD90 and CD15, it being rather improbable that these markers are also suitable as markers for NPC. The most promising markers are W4A5 and 57D2 which do not overall react with bone marrow populations. The antigens defined by the antibodies W4A5, 57D2 and W8C3 represent excellent surface markers with exceptional specificity for NPC. Since these are expressed in particular on mainly nestin-positive NPC, they are evidently expressed selectively on immature NPC.

The invention claimed is:

1. A monoclonal antibody produced by the hybridoma cell line 57D2, deposited in accordance with the Budapest treaty under the number DSM ACC2568, or a fragment of the monoclonal antibody.

2. A hybridoma cell line which produces an antibody as claimed in claim 1.

3. A composition comprising the antibody or fragment of claim 1 in a carrier.

4. A composition comprising the antibody or fragment of claim 1; and a suitable diluent, solvent, stabilizer or combination thereof.

5. A kit comprising the antibody or fragment of claim 1.

6. A method for isolating neural progenitor cells with an antibody, comprising the following steps:
   a) contacting a sample of a cell suspension which comprises neural progenitor cells to the monoclonal antibody or fragment thereof as claimed in claim 1, and
   b) isolating those cells in the sample which bind to the monoclonal antibody or fragment thereof.

7. A method for identifying a neural progenitor cell with an antibody, comprising the following steps:
   a) contacting a sample of a cell suspension which comprises neural progenitor cells to the monoclonal antibody or fragment thereof as claimed in claim 1, and
   b) identifying those cells in the sample which bind to the monoclonal antibody or fragment thereof.

* * * * *